United States Patent
Fox

(10) Patent No.: US 9,635,748 B2
(45) Date of Patent: Apr. 25, 2017

(54) SYSTEMS AND METHODS FOR HIGH-SPEED RADIOGRAPHY WITH HIGH RESOLUTION IMAGING OF LARGE-AREA FIELDS

(71) Applicant: Varian Medical Systems, Inc., Palo Alto, CA (US)

(72) Inventor: Timothy R. Fox, Chicago, IL (US)

(73) Assignee: Varex Imaging Corporation, Salt Lake City, UT (US)

( * ) Notice: Subject to any disclaimer, the term of this patent is extended or adjusted under 35 U.S.C. 154(b) by 669 days.

(21) Appl. No.: 13/848,412

(22) Filed: Mar. 21, 2013

(65) Prior Publication Data

US 2014/0286476 A1 Sep. 25, 2014

(51) Int. Cl.
*H05G 1/60* (2006.01)
*G01N 23/04* (2006.01)
*A61B 6/00* (2006.01)

(52) U.S. Cl.
CPC .............. *H05G 1/60* (2013.01); *A61B 6/4225* (2013.01); *A61B 6/4266* (2013.01); *G01N 23/04* (2013.01)

(58) Field of Classification Search
CPC .... G01N 23/04; G01N 23/043; G01V 5/0016; G01V 5/0066; A61B 6/4225; A61B 6/4266; A61B 6/486
See application file for complete search history.

(56) References Cited

U.S. PATENT DOCUMENTS

| | | | | |
|---|---|---|---|---|
| 4,092,537 | A * | 5/1978 | Stewart | 378/51 |
| 4,933,961 | A * | 6/1990 | Rushbrooke et al. | 378/57 |
| 5,309,496 | A * | 5/1994 | Winsor | 378/98.2 |
| 6,385,287 | B1 * | 5/2002 | Dorner | A61N 5/1049 378/154 |
| 7,062,011 | B1 * | 6/2006 | Tybinkowski et al. | 378/57 |
| 2006/0043335 | A1 * | 3/2006 | Cheng et al. | 252/301.5 |
| 2011/0198503 | A1 * | 8/2011 | Koren | G01T 1/20 250/362 |
| 2011/0204247 | A1 * | 8/2011 | Kasai et al. | 250/370.11 |

OTHER PUBLICATIONS

Crolla, David, Automotive Engineering: Powertrain, Chassis System and Vehicle Body, (2009), pp. 569-572.*
Morton, Ian, "Engineers X-ray Crash Dummies", Automotive News Europe, (Dec. 8, 1997), from the Internet: <http://europe.autonews.com/article/19971208/ANE/712080843/engineers-x-ray-crash-dummies>.*

* cited by examiner

Primary Examiner — Glen Kao

(57) ABSTRACT

The present invention proposes a high speed radiographic system for use with megavolt linear-accelerator pulsed x-ray sources to produce video images of large-area fields. A linear accelerator is positioned above a field of view. X-ray photons are directed through an object of interest traveling and/or colliding within the field of view. A large area scintillator system, either truly continuous or in large continuous adjacent pieces, converts the x-ray photons that pass through the object into visible light, and an arrangement of cameras, focused at that plane, where each camera sees a sub-area of the entire scintillator, and these sub-areas overlap somewhat to cover the entire scintillator. The resulting images generated in each camera are synchronized to produce one contiguous, synchronized stream of images.

26 Claims, 7 Drawing Sheets

Exemplary Computer
System 100

Exemplary Computer
System 300

Exemplary Computer System 700

SYSTEMS AND METHODS FOR HIGH-SPEED RADIOGRAPHY WITH HIGH RESOLUTION IMAGING OF LARGE-AREA FIELDS

BACKGROUND OF THE INVENTION

Radiography is the use of ionizing radiation (such as x-rays) to create internal images of an object or body. By using the physical properties of the irradiating particles, an image can be developed of the target that displays areas of various densities and compositions. Applications of radiography include medical radiography and industrial radiography.

Industrial radiography is a technique used to inspect materials for hidden flaws by using the ability of energetic x-rays and gamma rays to penetrate various materials. A typical configuration for a radiographic device includes a radiation source for emitting the radiation (e.g., x-rays) used for imaging and one or more radiation detectors corresponding to the radiation source for collecting incoming radiation after passing through the target volume. The particles collected by the detectors are subsequently used to generate a display (i.e., one or more images) of the targeted volume.

Generally, the detectors used for x-rays are usually of the scale of the size of the object being imaged. These detectors often comprise electronic circuits in the form of amorphous-silicon (a-Si) thin film transistor (TFT)/photodiode arrays (converters) coupled to radiation scintillators. Scintillators are used as detectors of radiation due to their inherent capability of converting incident radiation into lower-energy photons, e.g., visible light.

A natural extension of industrial radiography techniques for generating discrete images is using the same configuration in the generation of multiple images rapidly in a sequence, which when combined chronologically, can be viewed as a video. Conventionally, flat panel x-ray detectors are popular in industrial radiography applications due to their lower space requirements and generally adequate capabilities. However, flat panel detectors are often limited in frame rate and maximum area. Moreover, due to electrical connections along borders of the rectangular active area, they cannot be configured together to tesselate a plane without gaps between rectangular areas for larger fields of view (e.g., one or more square meters). For these reasons, flat panel detectors are unsuited for high speed radiography of large fields of view.

Another possible solution replaces flat panel x-ray detectors in favor of discrete-channel x-ray detectors. Discrete channel x-ray detectors are commercially available that operate at very high frame rates but are impractically expensive for large areas. Discrete channel detectors can be extremely fast, and can have very good x-ray detection efficiency, but with electronics required for each pixel the cost becomes prohibitively high for square meters of coverage Yet another x-ray imaging system uses vacuum tube image intensifiers to improve light yield from x-ray input to optical output, but like discrete-channel x-ray detectors, they are not practical for larger fields of view. Single video camera systems are limited in the number of pixels per frame, and therefore the detector is essentially limited by the number of pixels in the camera system. One camera can image a large area detector, but the pixels will be larger, dividing the large area into the same number of pixels in the camera sensor. Commercially available image intensifiers are inherently fast enough for high speed video applications, but are inefficient detectors at megavolt energies and cannot be made large enough to cover larger areas either.

SUMMARY OF THE INVENTION

This Summary is provided to introduce a selection of concepts in a simplified form that are further described below in the Detailed Description. This Summary is not intended to identify key features or essential features of the claimed subject matter, nor is it intended to be used to limit the scope of the claimed subject matter.

An embodiment of the present invention proposes a high speed radiographic system for use with megavolt linear-accelerator pulsed x-ray sources to provide video images of large-area fields. A linear accelerator is positioned above a field of view. X-ray photons are directed through an object or objects of interest traveling and/or colliding within the field of view. A large area scintillator system, either truly continuous or in large continuous adjacent pieces, converts the x-ray photons that pass through the object into visible light, and an arrangement of cameras are focused at that plane so that each camera sees a sub-area of the entire scintillator, and these sub-areas overlap somewhat to cover the entire scintillator. The frame rate of the produced video images is coherent with the pulse rate of the linear accelerator, and the field-of-view and spatial sampling of the generated images are determined by the number of cameras used and the magnification of the lens system that couples each camera to a portion of the field. In a further embodiment, the light output from the scintillator system is reflected by a mirror at an angle to the cameras, and the cameras record the reflection, thereby minimizing any radiation damage to the cameras due to incident radiation. In still further embodiments, the cameras are arranged in a two-dimensional array with fields of view that overlap each other. The resulting images generated in each camera are synchronized to produce one contiguous, synchronized stream of images.

In another embodiment, if radiation damage to the cameras is irrelevant, the camera array can be mounted directly under the detector at a closer working distance, which can improve the optical efficiency and reduce the overall size of the system. Depending on required field size and pixel spacing in the field, the camera array can be changed. Rectangular sensors in the cameras will work best with a rectangular array, rather than a hexagonal array for circular sensors.

In still further embodiments, a small-diameter optical image intensifier, such as are used in night-vision systems, may be added between each lens and its camera to increase the light hitting the camera sensor. Since the spacing between cameras is larger than the size of the lens and camera, this allows the night-vision apparatus to be fit on the camera without interference with neighboring cameras. So long as the number of photons or electrons at each interface in the chain (foil, scintillator, intensifier, sensor) is greater than the original number of x-ray photons stopped at the beginning of the chain, there will not be any degradation in the statistical signal to noise ratio. However, increasing the optical power into the camera sensor may be needed if the electronic noise in the sensor is too high compared with the signal produced by the relatively weak light hitting it.

BRIEF DESCRIPTION OF THE DRAWINGS

The accompanying drawings are incorporated in and form a part of this specification. The drawings illustrate embodiments. Together with the description, the drawings serve to explain the principles of the embodiments.

DETAILED DESCRIPTION

Figure 1:
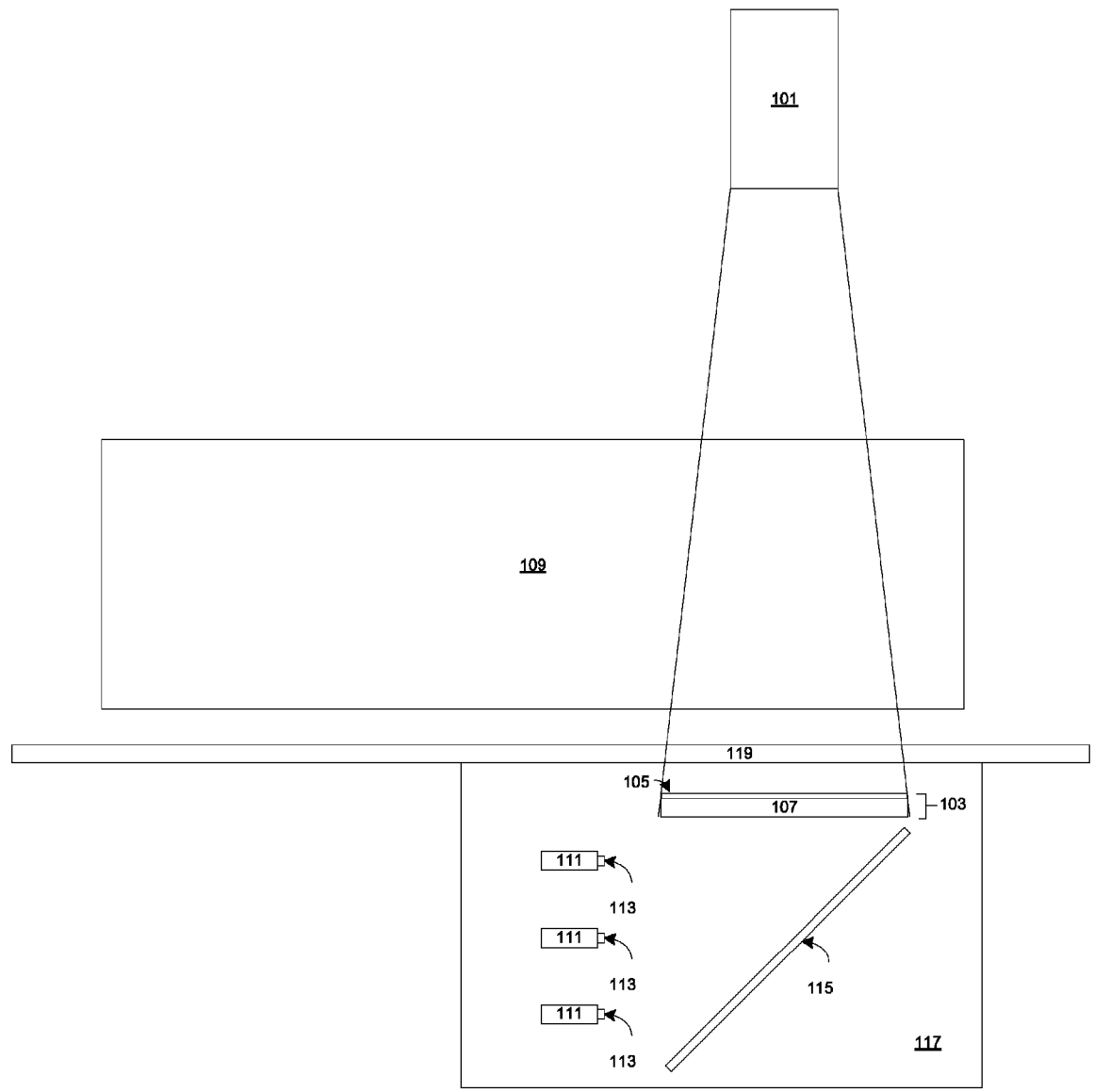
FIG. 1 depicts a block diagram of the bottom view of an exemplary digital imaging system, in accordance with various embodiments of the present invention.

Reference will now be made in detail to the preferred embodiments of the claimed subject matter, a method and system for the use of a radiographic system, examples of which are illustrated in the accompanying drawings. While the claimed subject matter will be described in conjunction with the preferred embodiments, it will be understood that they are not intended to limit these embodiments. On the contrary, the claimed subject matter is intended to cover alternatives, modifications and equivalents, which may be included within the spirit and scope as defined by the appended claims.

Furthermore, in the following detailed descriptions of embodiments of the claimed subject matter, numerous specific details are set forth in order to provide a thorough understanding of the claimed subject matter. However, it will be recognized by one of ordinary skill in the art that the claimed subject matter may be practiced without these specific details. In other instances, well known methods, procedures, components, and circuits have not been described in detail as not to obscure unnecessarily aspects of the claimed subject matter.

Some portions of the detailed descriptions which follow are presented in terms of procedures, steps, logic blocks, processing, and other symbolic representations of operations on data bits that can be performed on computer memory. These descriptions and representations are the means used by those skilled in the data processing arts to most effectively convey the substance of their work to others skilled in the art. A procedure, computer generated step, logic block, process, etc., is here, and generally, conceived to be a self-consistent sequence of steps or instructions leading to a desired result. The steps are those requiring physical manipulations of physical quantities. Usually, though not necessarily, these quantities take the form of electrical or magnetic signals capable of being stored, transferred, combined, compared, and otherwise manipulated in a computer system. It has proven convenient at times, principally for reasons of common usage, to refer to these signals as bits, values, elements, symbols, characters, terms, numbers, or the like.

It should be borne in mind, however, that all of these and similar terms are to be associated with the appropriate physical quantities and are merely convenient labels applied to these quantities. Unless specifically stated otherwise as apparent from the following discussions, it is appreciated that throughout the present claimed subject matter, discussions utilizing terms such as "storing," "creating," "protecting," "receiving," "encrypting," "decrypting," "destroying," or the like, refer to the action and processes of a computer system or integrated circuit, or similar electronic computing device, including an embedded system, that manipulates and transforms data represented as physical (electronic) quantities within the computer system's registers and memories into other data similarly represented as physical quantities within the computer system memories or registers or other such information storage, transmission or display devices.

Accordingly, embodiments of the claimed subject matter provide a method and system for cost-effective, high speed radiography for use with megavolt linear-accelerator pulsed x-ray sources to produce video images of large-area fields.

Digital Imaging System

FIG. 1 depicts a block diagram of the side view of an exemplary digital imaging system 100, in accordance with various embodiments of the claimed subject matter. Digital imaging systems such as those depicted in FIG. 1 may include one or more radiation sources 101. While embodiments are described herein to include a megavolt (MV) radiation source, it is to be understood that embodiments are well suited to alternate radiation sources, such as kilovolt (kV) radiation sources. In alternate embodiments, one or more of the radiation sources may be operable to generate both kV and MV radiation. According to some embodiments, the radiation source 101 may be implemented as a linear accelerator capable of generating a beam of x-ray particles at a given frequency (i.e., pulse rate). Other radiation sources may include alternate pulsed MV sources such as betatrons, and even non-pulsed (DC) x-ray sources.

As depicted in FIG. 1, digital imaging system 100 includes a detector 103 positioned for the reception of the x-ray beams generated by the radiation source 101. According to some embodiments, the detector 103 may include a converter 105 capable of converting a substantial fraction of the x-ray energy into energetic electrons. The detector 103 may also include a scintillating screen 107 in proximate contact with the converter 105, and which emits light photons from the converted electron kinetic energy, usually in the visible light region of wavelength, that can be imaged by a plurality of image acquisition devices 111 (still or video).

In some embodiments, the detector 103, image acquisition devices 111 and reflective surface 115 may be housed in a contained volume 117, such as a shelter or pit with a upper surface 119. According to such embodiments, the imaging subject 109 may be configured to travel over the surface 119 of the contained area 117, passing through an x-ray beam from a linear-accelerator source 101 above the subject 109 to a rectangular area detector 103 housed in the contained area 117 below the vehicle. The ensemble of cameras 111 (which may consist of a single camera, according to various embodiments) produces image data from the light emitted from the detector side away from the vehicle 109. In still further embodiments, a second object—such as a stationary target or movement-controlled target—may be positioned either over a portion of the projected beam or at some pre-defined distance out of the projected beam so as to facilitate or simulate a collision with the imaging subject 109. The resultant impact and damage to the imaging subject 109 within the projected beam can therefore be imaged, either as a sequence of discrete images or a video sequence.

According to some embodiments, the image acquisition devices 111 may be implemented as a plurality of cameras, arranged in a two dimensional array. As depicted in FIG. 1, the digital imaging system 100 also includes an optical system. As presented, the optical system is positioned between the scintillator 107 and image acquisition devices 111, and may include a imaging lens 113 on each image acquisition device 111. In some embodiments, the image acquisition devices 111 may be positioned to capture, through the imaging lens 113, images of the light output from the scintillator 107 resulting from the reception of the irradiating particles from the radiation source 101. In an embodiment, the image acquisition devices 111 may be positioned to to receive the light output directly (e.g., in-line with the radiation source 101 and scintillator 107. In alternate embodiments, the image acquisition devices 111 may be positioned such that the image acquisition devices 111 are not directly within the beam of irradiating particles projected by the radiation source 101. In such (optional) embodiments, a reflective surface 115—such as a mirror—may be positioned so as to reflect the light photons produced by the detector 103, with the image acquisition devices 111 capturing images of the reflection in the reflective surface 115, thereby avoiding any potential damage to the image acquisition devices 111 resulting from incidental absorption of particles from the irradiating beam.

In further embodiments, imaging lens 113 may be configured to focus on the detector 103 or the reflection of the detector 103 at a pre-defined magnification. Additionally, imaging lens 113 may include optical image intensifiers, such as night-vision apparatuses (not shown) to increase the amount of light received by the image acquisition device 111. As spacing between each image acquisition device 111 will typically be larger than the sizes of the lens and camera, image intensifying apparatuses may be fit on the camera without interference to neighboring cameras.

Figure 2:
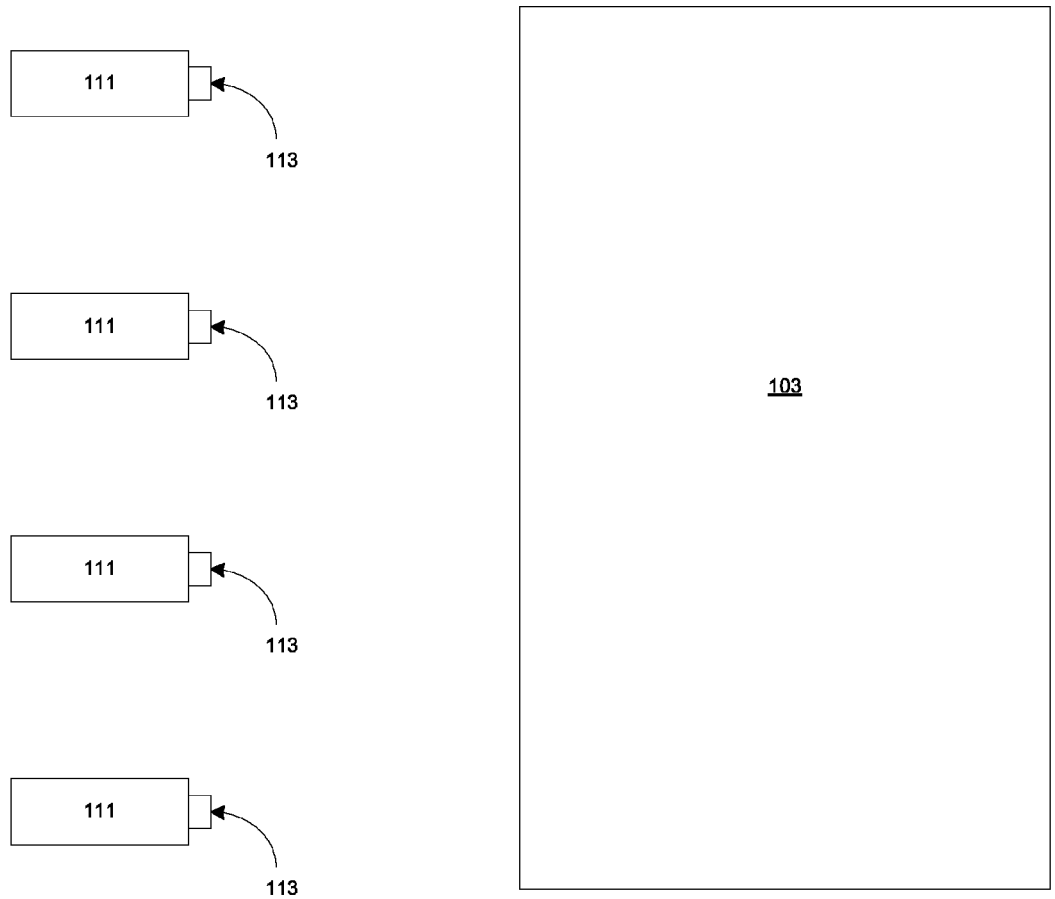
FIG. 2 is a block diagram of the side view of an exemplary digital imaging system, in accordance with various embodiments of the present invention.

FIG. 2 depicts a block diagram of the bottom view of an exemplary digital imaging system, such as the digital imaging system 100 described above and depicted in FIG. 1. As presented in FIG. 2, digital imaging system 100 includes a radiation detector 103, image acquisition devices 111 and an optical system (presented herein as imaging lenses 113). According to some embodiments, the image acquisition devices 111 may be arranged in a two dimensional array. In FIGS. 1 and 2, the image acquisition devices 111 are presented in a two-dimensional array of different values according to varying axes. For example, the image acquisition devices 111 depicted in FIGS. 1 and 2 are arranged in a 3×4 arrangement (3 rows, 4 columns). The image acquisition devices 111 are thus depicted as 3 image acquisition devices (cameras) in the side view of the system presented in FIG. 1, and 4 image acquisition devices (cameras) in the bottom view of the system presented in FIG. 2.

While the claimed subject matter is described in a 3×4 arrangement, it is to be understood that such a depiction is solely for exemplary purposes and that the claimed subject matter is in no way limited to such arrangements. Indeed, the claimed subject matter is well suited to alternate embodiments that include arrangements with a varying number of image acquisition devices along either the horizontal and/or vertical axes. In still further embodiments, the number of image acquisition devices along either the horizontal and/or vertical axes is scalable between usages to fit particular needs (e.g., larger or smaller fields of view). For example, the number and/or arrangement of the image acquisition devices may be modified by adding or removing image acquisition devices between usages.

Timing and Synchronization System

Figure 3:
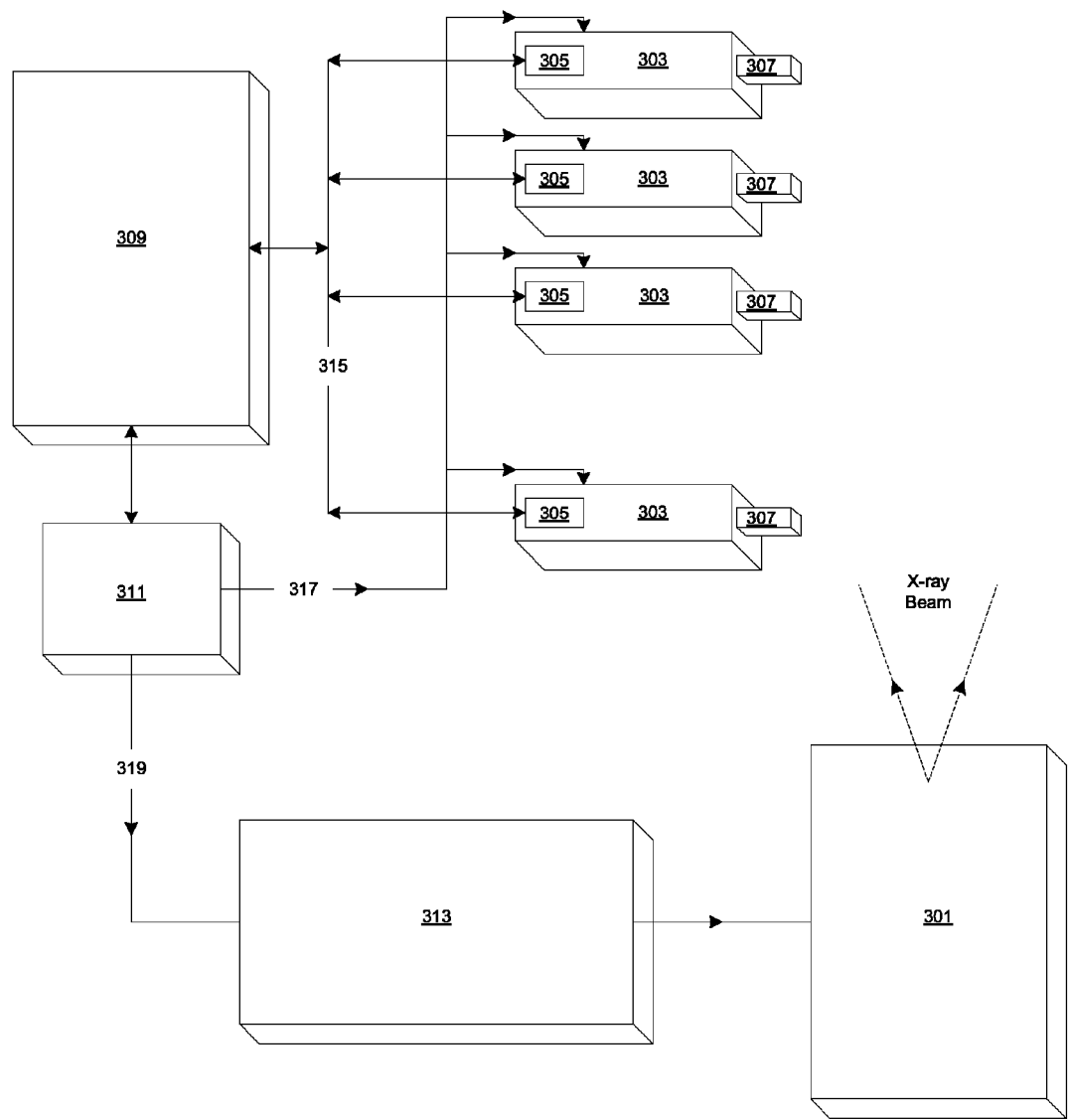
FIG. 3 is a block diagram of a synchronizing system for an exemplary digital imaging system, in accordance with various embodiments of the present invention.

According to various aspects of the claimed subject matter, the images generated by the plurality of image acquisition devices (e.g., cameras 111) are combined and processed to produce synchronized, large-field images (and/or a video). Synchronization may be performed with a timing system which includes one or more processing devices. FIG. 3 depicts an exemplary timing system 300 which, when used with the imaging systems described above with respect to FIGS. 1 and 2 (e.g., imaging system 100, 200), can be configured to perform synchronization of a plurality of generated images to produce a large field image or video. As depicted in FIG. 3, a plurality of image acquisition devices 303 generates images of emitted photons from an x-ray detector (not shown). The emitted photons, as described above, are generated by the reception of x-ray particles in the x-ray detector from an x-ray beam projected by an x-ray source (301) that have travelled through an imaging subject (not shown).

According to some embodiments, the images generated in the plurality of image acquisition devices 303 are produced by receiving emitted light photons in sensors disposed within the image acquisition devices 303. Optical systems 307 including camera lens and/or night vision apparatuses may be used to direct, focus, and/or modify the number of photons received by the sensor in the image acquisition devices. In some embodiments, the generated images may be stored in internal memory devices 305 disposed in each image acquisition device 303. As presented in FIG. 3, the memory devices 305 of the image acquisition devices 303 may be communicatively captured in imaging device 309. According to some embodiments, imaging device 309 may be implemented as a computing system either proximately or remotely located with respect to the image acquisition devices 303, and communicatively coupled to the image acquisition devices 303 via a bilateral connection (e.g., a bus) in a data network. As depicted in FIG. 3, image data stored in the memory devices 305 of the imaging acquisition devices 303 may be transmitted to the imaging device 309 via a camera data and control bus 317. According to an embodiment, the imaging computer may download the stored images from the memory devices 305 once an imaging session is completed. For example, for an imaging session which comprises one or more simulated collisions, the stored image data may be downloaded once the one or more simulated collisions are completed. In alternate embodiments, the imaging computer may receive the images as they are generated in the image acquisition devices 303 in real-time (or approximate real-time). In still further embodiments, the imaging computer may download the image data from the memory devices 305 according to a (pre-defined) schedule.

In one embodiment, the schedule may be maintained and administered via a timing device 311 communicatively coupled to both the imaging device 309, the image acquisition devices 303. In still further embodiments, the timing device 311 may also be communicatively coupled to an accelerator control and modulator system 313, operable to control the generation of the x-ray beams in the linear accelerator x-ray source 301. According to such implementations, the timing device 311 may be operable to coordinate and synchronize timing of events within the imaging system depicted in FIGS. 1 and 2 and described above. Thus, for example, the timing device 311 may be operable to send data to the accelerator control and modulator system 313 to begin (or end) generation of an x-ray beam in linear accelerator x-ray source 301. As depicted in FIG. 3, this data may be transmitted through a modulator control and timing bus 319 communicatively coupling the timing device 311 with the accelerator control and modulator system 313. The timing device 311 then (either immediately, upon user command, or after a pre-defined period of time) sends instructions to the image acquisition devices 303 to begin generating images from received light photons generated from the x-ray beam produced by the linear accelerator x-ray source 301.

In one embodiment, the instructions to the image acquisition devices 303 may be delivered via a camera synchronization bus 317. The image acquisition devices 303 may generate images continuously, based on the characteristics of the particular image acquisition device, or may generate images at pre-timed intervals. According to an embodiment, two or more of the image acquisition devices may be instructed, via the timing device 311, to generate images simultaneously. In further embodiments, each generated image is individually time stamped, (e.g., internally by the image acquisition device 303). According to still further embodiments, timing device 311 is also operable to transmit data to imaging device 309 to begin downloading of image data stored in memory devices 305 in the image acquisition devices 303 (e.g., when image acquisition is stopped or paused) or end downloading of the image data (e.g., when image acquisition begins or resumes).

Once the image data is received in the imaging device 309, the generated images from the image acquisition devices 303 may be combined and synchronized. That is, generated images with equivalent time stamps or other such imputed chronological association may be combined, with redundancies in the generated images due to overlapping fields of view eliminated or reduced, thereby generating a single contiguous large field image per time unit. Each image acquisition device 303 may be mapped specifically to a portion of the x-ray detector. The acquired images that contain the portions of the x-ray detector corresponding to multiple image acquisition devices 303 (e.g., overlapping portions) may, in such instances, be resolved such that duplicates of overlapping portions are combined or removed from the synchronized image. The synchronized large field images can then be sequenced, chronologically, to produce a video of the x-ray images.

Detector Signal Sequence

Figure 4:
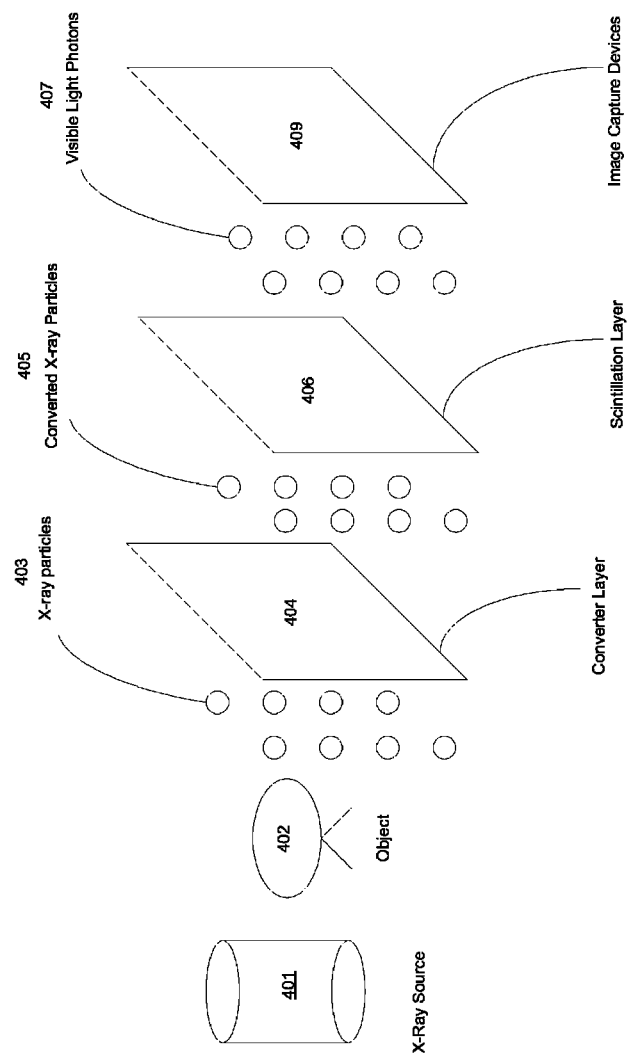
FIG. 4 is a diagram of an exemplary particle sequence, in accordance with various embodiments of the present invention.

FIG. 4 depicts an illustration of an image detector signal sequence 400, in accordance with embodiments of the present invention. The x-ray source 401 sends a beam of x-ray photons through an object 402. X-ray photons 403 that are not absorbed by the object 402, strike a layer of converting material 404, which converts some of the x-ray energy into energetic electrons 405. In some embodiments, the converter 404 may be implemented as an intensifying screen (or foil) of a suitable metallic material that is thick enough to stop some of the megavolt x-ray photons and thin enough to allow the resulting energetic electrons to escape in the forward direction. The unabsorbed photons and energetic electrons from this conversion then strike a layer of scintillating material 406, that emits light 407 of an intensity related to the amount of x-rays absorbed by the foil and scintillator. Images of the emitted light are then produced by image acquisition devices 409, either by receiving the emitted light photons in sensors located within the image acquisition devices or, optionally, via reflection of the emitted light in a reflected surface.

Figure 5:
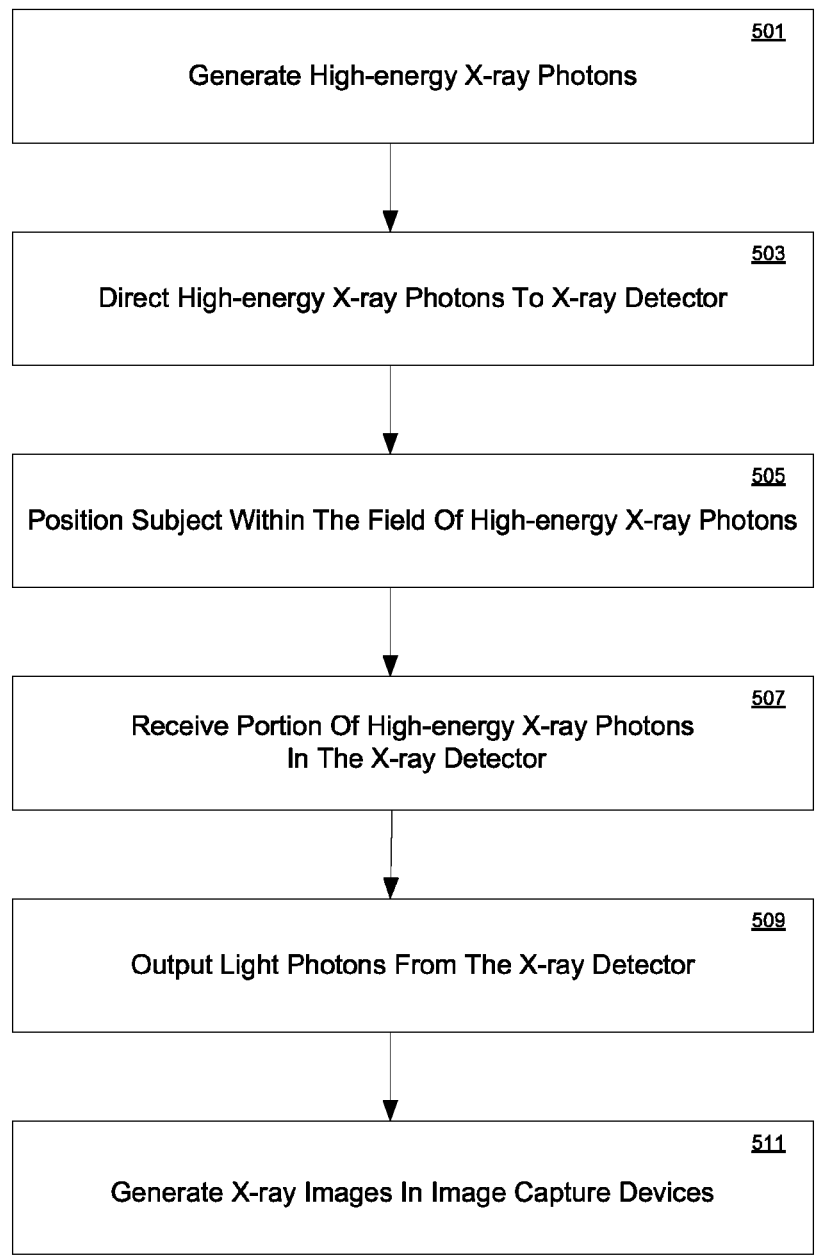
FIG. 5 is a flow diagram of a process for generating an X-ray video, in accordance with various embodiments of the present invention.

FIG. 5 depicts an example procedure 500 for generating large field x-ray images and videos with high speed image acquisition devices. Steps 501-511 describe exemplary steps of the process 500 in accordance with the various embodiments herein described.

At step 501, a plurality of x-ray particles (photons) are generated. Generation of the x-ray particles may be performed in a linear accelerator x-ray source (e.g., linear accelerator X-ray Source 301 of FIG. 3), and controlled by an accelerator control and modulator system (e.g., accelerator control and modulator system 313 of FIG. 3). According to one aspect, generation of the x-ray particles may be initiated according to a schedule and/or based on user input, via a timing device (e.g., timing device 311 of FIG. 3). In some embodiments, the x-ray particles comprise high energy (megavolt) x-rays At step 503, the (high energy) x-ray particles generated at step 501 are directed to an x-ray detector (e.g., x-ray detector 103 of FIGS. 1 and 2). The x-ray particles may, for example, be directed as a continuous beam of x-ray particles encompassing a field emanating from the x-ray source to the x-ray detector. At step 505, an imaging subject is positioned within the field of emitted x-ray particles. In some embodiments, the subject may be positioned through controlled movement of the subject into (and/or through) the field of emitted x-ray particles. Alternately, the subject may be pre-positioned prior to the generation and emission of the x-ray particles and stationary during all or a portion of the x-ray particle emission. Alternately, the subject may be positioned by directing the subject to a designated point within the field of emitted x-ray particles. In still further embodiments, a collision between the imaging subject and a secondary object (e.g., either a stationary object or another controlled movement object) may be facilitated during step 505. In some embodiments, the collision may be triggered within the field of emitted x-ray particles. Alternately, the collision may occur at a pre-defined distance outside the field of emitted x-ray particles. Movement of the imaging subject and/or the secondary object may be controlled according to various methods including, but not limited to: radio control; pre-programmed routes; and/or track, rail, cable or other such guidance systems.

At step 507, the portion of the high energy x-ray particles emitted in step 501 that were not absorbed by the imaging subject at step 505 are received in the x-ray detector. Once received, a portion of the x-ray particles are converted into energetic electrons by a converter layer disposed within the x-ray detector. The actual amount of converted particles depends in part on the characteristics of the converter. The kinetic energy of the energetic electrons and the energy deposited from the x-ray photons not absorbed in the converter cause a scintillator layer in the detector to emit light photons at step 509. At step 511, one or more images are acquired of the emission of the light photons from the scintillator in the x-ray detector at step 509. Image acquisition may be performed, for example, by receiving, in a sensor of an image acquisition device (such as a camera, or other image acquisition device 303 depicted in FIG. 3 and described above). Subsequently, the acquired images may be stored (in an on-board memory device of the image acquisition device, for example) and downloaded to an imaging device (e.g., imaging device 309 in FIG. 3). The imaging device may then synchronize acquired images from multiple image acquisition devices which correspond to equivalent times by combining the images and removing overlapping portions. In this manner, large field X-ray images and videos can be efficiently produced with high speed image acquisition devices without requiring prohibitively expensive equipment.

Exemplary Image Acquisition Device

Figure 6:
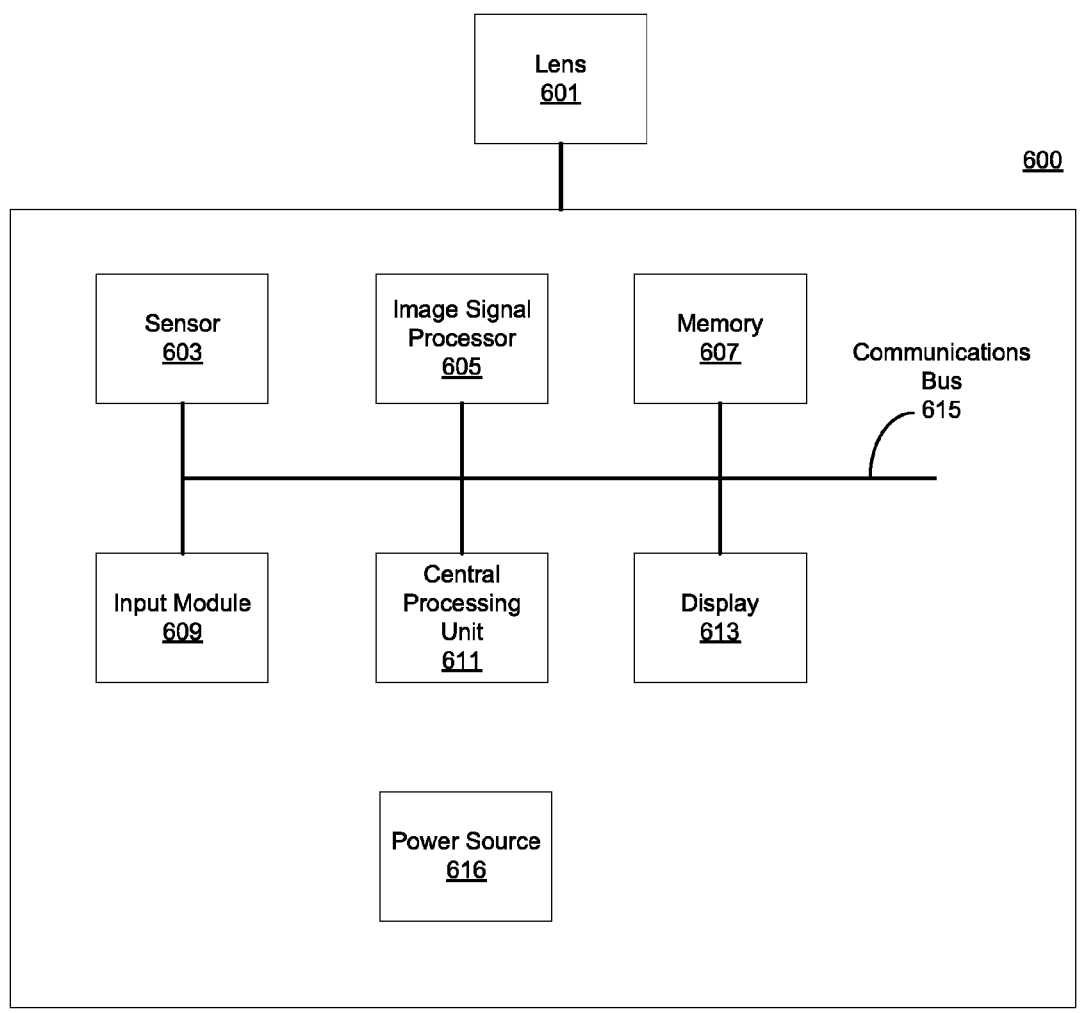
FIG. 6 depicts an exemplary image acquisition device, in accordance with embodiments of the present invention.

FIG. 6 depicts an illustration of an exemplary image acquisition device 600 in accordance with one embodiment of the present invention. Although specific components are disclosed in image acquisition device 600 it should be appreciated that such components are examples. That is, embodiments of the present invention are well suited to having various other components or variations of the components recited in image acquisition device 600. It is appreciated that the components in image acquisition device 600 may operate with other components other than those presented, and that not all of the components of image acquisition device 600 may be required to achieve the goals of image acquisition device 600.

In a typical embodiment, image acquisition device 600 includes sensor 603, image signal processor (ISP) 605, memory 607, input module 609, central processing unit (CPU) 611, display 613, communications bus 615, and power source 616. Power source 616 supplies power to image acquisition device 600 and may, for example, be a DC or AC power source. CPU 611 and the ISP 605 can also be integrated into a single integrated circuit die and CPU 611 and ISP 605 may share various resources, such as instruction logic, buffers, functional units and so on, or separate resources may be provided for image processing and general-purpose operations. Image acquisition device 600 can be implemented as, for example, a digital camera, webcam, video device (e.g., camcorder), or similar image/video acquisition devices capable of high-speed image acquisition.

Sensor 603 receives light via a lens 601 and converts the light received into a signal (e.g., digital or analog). According to some embodiments, lens 601 may be permanently attached to the image acquisition device 600. Alternatively, lens 601 may be detachable and interchangeable with lens of other properties. These properties may include, for example, focal lengths, apertures and classifications. In typical embodiments, lens 601 may be constructed of glass, though alternate materials such as quartz or molded plastics may also be used. Sensor 603 may be any of a variety of optical sensors including, but not limited to, complementary metal-oxide-semiconductor (CMOS) or charge-coupled device (CCD) sensors. Sensor 603 is coupled to communications bus 615 and may provide image data received over communications bus 615. In further embodiments, sensor 603 includes light intensity sensing capability, and the image data received may include data corresponding to the determined intensity of the light in a scene or image.

Image signal processor (ISP) 605 is coupled to communications bus 615 and processes the data generated by sensor 603. More specifically, image signal processor 605 processes data from sensor 602 for storing in memory 607. For example, image signal processor 605 may compress and determine a file format for an image to be stored in within memory 607.

The input module 609 allows the entry of user-input into image acquisition device 600 which may then, among other things, control the sampling of data by sensor 603 and subsequent processing by ISP 605. Input module 609 may include, but is not limited to, navigation pads, keyboards (e.g., QWERTY), buttons, touch screen controls (e.g., via display 613) and the like.

The central processing unit (CPU) 611 receives commands via input module 609 and may control a variety of operations including, but not limited to, sampling and configuration of sensor 603, processing by ISP 605, and management (e.g., the addition, transfer, and removal) of images and/or video from memory 607.

Exemplary Computing System

Figure 7:
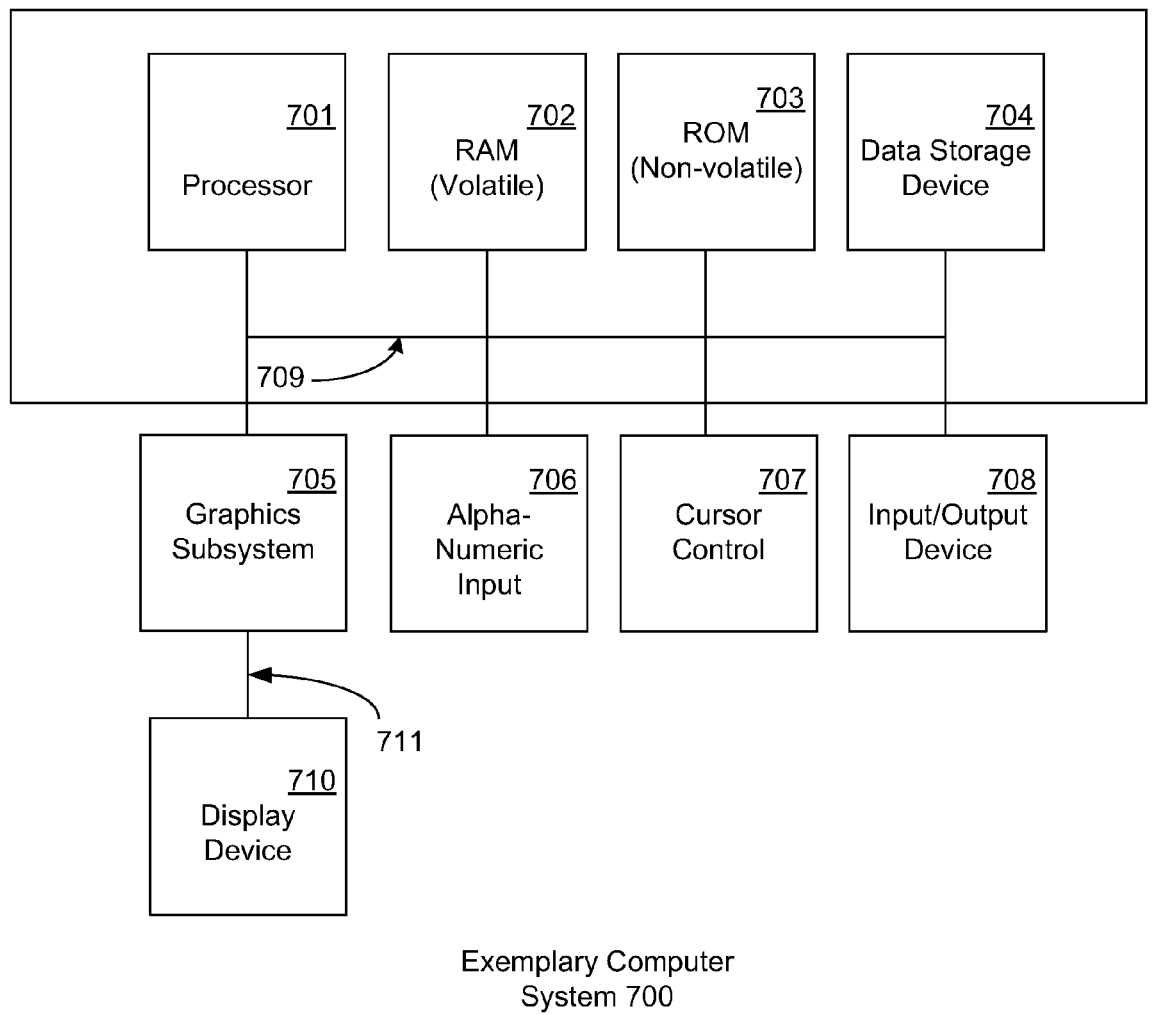
FIG. 7 depicts an exemplary computing environment, in accordance with embodiments of the present invention.

As presented in FIG. 7, an exemplary system 700 upon which embodiments of the present invention may be implemented includes a general purpose computing system environment. Imaging device 309, depicted in FIG. 3 and described above may, for example, be implemented as a computing system. In its most basic configuration, computing system 700 typically includes at least one processing unit 701 and memory, and an address/data bus 709 (or other interface) for communicating information. Depending on the exact configuration and type of computing system environment, memory may be volatile (such as RAM 702), non-volatile (such as ROM 703, flash memory, etc.) or some combination of the two.

Computer system 700 may also comprise an optional graphics subsystem 705 for presenting information to the computer user, e.g., by displaying information on an attached display device 710, connected by a video cable 711. According to embodiments of the present claimed invention, the graphics subsystem 705 may be coupled directly to the display device 710 through the video cable 711. A graphical user interface of an application for displaying images generated by a medical imaging device described above with respect to FIG. 1, and executing in the computer system 700 may be generated in the graphics subsystem 705, for example, and displayed to the user in the display device 710. In alternate embodiments, display device 710 may be integrated into the computing system (e.g., a laptop or netbook display panel) and will not require a video cable 711. In one embodiment, the processing of the image data acquired in the sensors (603 of FIG. 6) to generate an image may be performed, in whole or in part, by graphics subsystem 705 in conjunction with the processor 701 and memory 702, with any resulting output displayed in attached display device 710.

Additionally, computing system 700 may also have additional features/functionality. For example, computing system 700 may also include additional storage (removable and/or non-removable) including, but not limited to, magnetic or optical disks or tape. Such additional storage is illustrated in FIG. 7 by data storage device 707. Computer storage media includes volatile and nonvolatile, removable and non-removable media implemented in any method or technology for storage of information such as computer readable instructions, data structures, program modules or other data. RAM 702, ROM 703, and data storage device 707 are all examples of computer storage media.

Computer system 700 also comprises an optional alphanumeric input device 706, an optional cursor control or directing device 707, and one or more signal communication interfaces (input/output devices, e.g., a network interface card) 709. Optional alphanumeric input device 706 can communicate information and command selections to central processor 701. Optional cursor control or directing device 707 is coupled to bus 709 for communicating user input information and command selections to central processor 701. Signal communication interface (input/output device) 709, also coupled to bus 709, can be a serial port. Communication interface 709 may also include wireless communication mechanisms. Using communication interface 709, computer system 700 can be communicatively coupled to other computer systems over a communication network such as the Internet or an intranet (e.g., a local area network), or can receive data (e.g., a digital television signal).

In the foregoing specification, embodiments have been described with reference to numerous specific details that may vary from implementation to implementation. Thus, the sole and exclusive indicator of what is the invention, and is intended by the applicant to be the invention, is the set of claims that issue from this application, in the specific form in which such claims issue, including any subsequent correction. Hence, no limitation, element, property, feature, advantage, or attribute that is not expressly recited in a claim should limit the scope of such claim in any way. Accordingly, the specification and drawings are to be regarded in an illustrative rather than a restrictive sense.

What is claimed is:

1. A system, comprising:
an x-ray source, configured to generate high-energy x-ray photons;
an x-ray detector comprising a converter and a scintillator, the x-ray detector being configured to receive the high-energy x-ray photons from the source, to convert the high-energy x-ray photons into a plurality of light photons;
a plurality of image acquisition devices arranged in a two-dimensional array with overlapping fields of view, each image acquisition device of the plurality of image acquisition devices being configured to generate a plurality of x-ray images of a moving object crossing between the x-ray source and the x-ray detector at a high rate of speed from the plurality of light photons produced by the x-ray detector;
a central control circuit configured to combine the plurality of x-ray images captured by the plurality of image acquisition devices into a set of combined x-ray images;
a timing device disposed in the central control circuit and communicatively coupled to the x-ray source and the plurality of image acquisition devices, the timing device being configured to synchronize a timing of the generation of the high-energy x-ray photons in the x-ray source with the generation of x-ray images by the plurality of image acquisition devices; and
a reflective surface positioned to reflect the plurality of light photons produced by the x-ray detector to a plurality of sensors included in the plurality of image acquisition devices.

2. The system according to claim 1, wherein the x-ray source comprises a linear accelerator.

3. The system according to claim 1, wherein the x-ray source comprises a pulse x-ray source configured to generate the high-energy x-ray photons at a pre-determined pulse rate.

4. The system according to claim 1, wherein the system further comprises a metal converting film disposed over the scintillator and configured to increase an efficiency of the scintillator.

5. The system according to claim 1, wherein the plurality of image acquisition devices comprises a plurality of high-speed video cameras.

6. The system according to claim 1, further comprising a contained volume, wherein the moving object travels along a surface of the contained volume.

7. The system according to claim 6, wherein the x-ray detector, the mirror, and the plurality of image acquisition devices are positioned within the contained volume.

8. The system according to claim 1, wherein a plurality of redundancies in the generated images caused by the overlapping fields of view are reduced by the central control circuit during combination to generate a single contiguous large field image per time unit.

9. The system according to claim 1, wherein the plurality of image acquisition devices comprises a plurality of memory devices, wherein the plurality of x-ray images generated by the plurality of image acquisition devices is stored in the plurality of memory devices.

10. The system according to claim 9, wherein the central control circuit combines the plurality of x-ray images captured by the plurality of image acquisition devices by accessing the plurality of x-ray images stored in the plurality of memory devices and combining the plurality of x-ray images into the set of combined x-ray images.

11. The system according to claim 10, wherein the central control circuit is remotely positioned with respect to the plurality of image acquisition devices.

12. The system according to claim 1, wherein the plurality of x-ray images compose a video.

13. The system according to claim 1, wherein the object comprises an automobile.

14. The system according to claim 13, further comprising a means for facilitating a collision with the automobile.

15. The system according to claim 14, wherein the plurality of image acquisition devices are configured to generate a plurality of x-ray images of a collision between the automobile and the means for facilitating a collision with the automobile.

16. A method comprising:
generating a plurality of high-energy x-ray photons in an x-ray source;
directing the plurality of high-energy x-ray photons as a field to an x-ray detector;
facilitating a collision between an automobile and an object within the field of high-energy x-ray photons;
receiving a portion of the plurality of high-energy x-ray photons from the x-ray source in the x-ray detector, the x-ray detector being positioned on an opposite side of the automobile from the x-ray source;
outputting, with a scintillator comprised in the x-ray detector, a plurality of light photons from the x-ray detector;
reflecting, with a reflective surface, the plurality of light photons from the x-ray detector to a plurality of sensors in a plurality of image acquisition devices; and
generating a plurality of x-ray images in the plurality of image acquisition devices from the plurality of light photons, the plurality of image acquisition devices being arranged in a two-dimensional array with overlapping fields of view,
wherein the generating the plurality of high-energy x-ray photons and the generating the plurality of x-ray images is synchronized by a timing device in a central control circuit communicatively coupled to the x-ray source and the plurality of image acquisition devices.

17. The method according to claim 16, further comprising combining the plurality of x-ray images generated in the plurality of image acquisition devices into a set of combined x-ray images.

18. The method according to claim 17, wherein generating the plurality of x-ray images in the plurality of image acquisition devices comprises storing the plurality of x-ray images in a plurality of memory devices corresponding to the plurality of image acquisition devices.

19. The method according to claim 18, wherein the combining the plurality of x-ray images comprises:
retrieving the stored plurality of x-ray images from the plurality of memory devices; and
combining the plurality of x-ray images with the timing device system.

20. The method according to claim 19, wherein the central control circuit is remotely positioned from the plurality of image acquisition devices.

21. A non-transitory computer readable medium containing program instructions embodied therein for causing a computer graphics system to generate x-ray images, the program instructions comprising:

instructions to generate a plurality of high-energy x-ray photons in an x-ray source;

instructions to direct the plurality of high-energy x-ray photons as a field to an x-ray detector;

instructions to facilitate a collision between an automobile and an object within the field of high-energy x-ray photons;

instructions to receive a portion of the plurality of high-energy x-ray photons from the x-ray source in the x-ray detector, the x-ray detector being positioned on an opposite side of the automobile from the x-ray source;

instructions to output, with a scintillator comprised in the x-ray detector, a plurality of light photons from the x-ray detector;

instructions to reflect, with a reflective surface, the plurality of light photons from the x-ray detector to a plurality of sensors comprised in a plurality of image acquisition devices; and instructions to generate a plurality of x-ray images in the plurality of image acquisition devices from the plurality of light photons, the plurality of image acquisition devices being arranged in a two-dimensional array with overlapping fields of view, wherein generation of the plurality of high-energy x-ray photons and generation of the plurality of x-ray images is synchronized by a timing device in a central control circuit communicatively coupled to the x-ray source and the plurality of image acquisition devices.

22. The non-transitory computer readable medium according to claim 21, further comprising instructions to combine the plurality of x-ray images generated in the plurality of image acquisition devices into a set of combined x-ray images.

23. The non-transitory computer readable medium according to claim 22, wherein the instructions to generate the plurality of x-ray images in the plurality of image acquisition devices comprises instructions to store the plurality of x-ray images in a plurality of memory devices corresponding to the plurality of image acquisition devices.

24. The non-transitory computer readable medium according to claim 23, wherein the instructions to combined the plurality of x-ray images comprises:

instructions to retrieve the stored plurality of x-ray images from the plurality of memory devices; and instructions to combine the plurality of x-ray images in the timing device.

25. The non-transitory computer readable medium according to claim 24, wherein the central control circuit is remotely positioned from the plurality of image acquisition devices.

26. The non-transitory computer readable medium according to claim 24, wherein the central control circuit comprises a computing device.

* * * * *